United States Patent [19]

Takamizawa et al.

[11] 4,085,128

[45] Apr. 18, 1978

[54] CYCLIC PHOSPHAMIDE DERIVATIVES

[75] Inventors: Akira Takamizawa; Tsuyoshi Iwata, both of Ibaraki, Japan

[73] Assignee: Shionogi & Co., Ltd., Osaka, Japan

[21] Appl. No.: 737,983

[22] Filed: Nov. 2, 1976

Related U.S. Application Data

[63] Continuation-in-part of Ser. No. 629,128, Nov. 5, 1975, abandoned.

[30] Foreign Application Priority Data

Nov. 20, 1974 Japan .................... 49-133257

[51] Int. Cl.² .................... C07C 143/68; A61K 31/255
[52] U.S. Cl. .................... 260/456 A; 260/953; 260/956; 424/303
[58] Field of Search .................... 260/456 A

[56] References Cited

U.S. PATENT DOCUMENTS 3,828,090  8/1974  Arnold et al. .................... 260/456 A

OTHER PUBLICATIONS

Brock et al., Areneim–Forsch (Drug Res.) 24(8), 1139 (1974).
Takamizawa et al., J. Med. Chem., 17, 1237 (1974).
Takamizawa et al. (I), J. Amer. Chem. Soc., 95, 985 (1973).
Takamizawa et al. (II), Tetrahedron Letters, No. 6, 517 (1974).

*Primary Examiner*—Nicky Chan
*Attorney, Agent, or Firm*—Wenderoth, Lind & Ponack

[57] ABSTRACT

Cyclic phosphamide derivatives of the general formula:

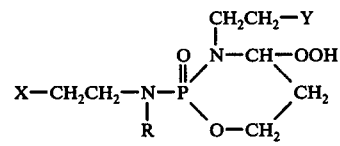

[wherein X represents a halogen atom, Y represents a lower alkanesulfonyloxy, and R represents a lower alkyl] being useful as medicaments exhibiting antitumor and immunosuppressive activities.

2 Claims, No Drawings

CYCLIC PHOSPHAMIDE DERIVATIVES

This application is a continuation-in-part of our pending application, Ser. No. 629,128, filed Nov. 5, 1975, now abandoned.

The present invention relates to cyclic phosphamide derivatives and process for production thereof. More particularly, it relates to novel and therapeutically valuable compounds having antitumor and immunosuppressive activities.

The objective compounds of the present invention may be represented by the following general formula:

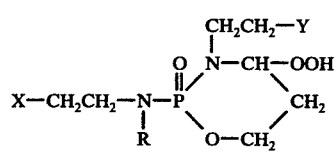

[wherein X represents a halogen atom, Y represents a lower alkanesulfonyloxy of 1-5 carbon atoms, and R represents a lower alkyl of 1-5 carbon atoms]

It had been attempted by the present inventors to chemically modify phosphorodiamidates for the purpose of developing antitumor agents of alkylating type, and discovered that a series of hydroperoxyoxazaphosphorine derivatives exhibit an excellently selective toxicity against the tumor cells (Japanese Public Inspection No. 48-86870). The investigation on the same series of compounds has been continued thereafter, and in consequence novel phosphorodiamidates exhibiting more potent anti-neoplastic action but less toxicity have been discovered by the present inventors. The present invention is based on this successful finding.

The objective compounds (I) can be prepared from phosphorodiamidates of the general formula (II) by oxidation with ozone.

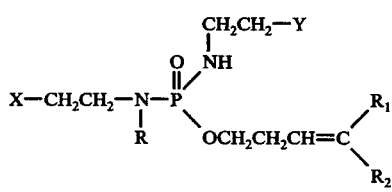

[wherein X, Y and R each has the same meaning as mentioned above; and $R_1$ and $R_2$ each represents a hydrogen atom, alkyl, aryl or aralkyl]

The definition in the above general formulae can be explained in more detail as follows. The halogen atoms indicated by X include chlorine, bromine, and iodine. The lower alkane-sulfonyloxy groups indicated by Y are those of 1-5 carbon atoms including methanesulfonyloxy, ethanesulfonyloxy, propanesulfonyloxy, and the like. The lower alkyls represented by R are those of 1-5 carbon atoms including methyl, ethyl, propyl, isopropyl, butyl, pentyl, and the like. The atoms or atomic groups represented by $R_1$ and $R_2$ may be optional groups insofar as they do not disturb the objective ozone oxidation of the double bond since they never participate in the structure of the objective compounds. Such groups may optionally be selected from hydrogen atom, alkyls (preferably those of 1-5 carbon atoms), aryls (preferably those of 6-10 carbon atoms) and aralkyls (preferably those of 7-10 carbon atoms).

The starting compounds (II) used in the present invention are novel ones which have not been described in any literature. For example, the compounds in which X is a chlorine and Y is a methanesulfonyloxy may be prepared as follows in accordance with the accompanied reaction scheme.

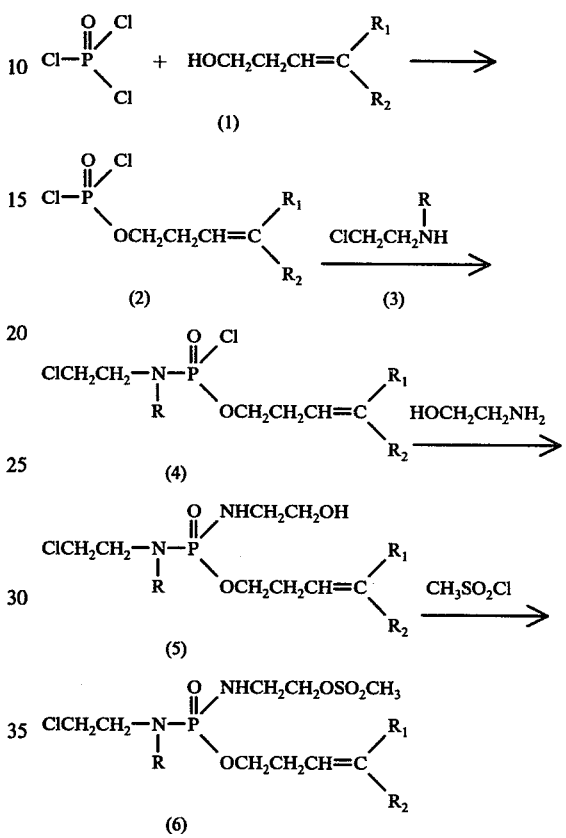

(wherein R, $R_1$ and $R_2$ each has the same meaning as defined above)

The starting 3-buten-1-ols (1) are subjected to reaction with phosphorus oxychloride in an inert solvent (e.g. dichloromethane) at a low temperature (usually about $-30°$ - $-20°$ C). The product (2) then without isolation is subjected to reaction with N-alkyl-2-chloroethylamines (3) in the same solvent as mentioned above in the presence of a base (e.g. triethylamine) at a low temperature (usually about $-40°$ - $-30°$ C). Thus resulting product (4) is then subjected to reaction with ethanolamine in an inert solvent (e.g. dichloromethane) in the presence of a base (e.g. triethylamine) at room temperature to yield the phosphorodiamidates (5). The latter is subjected to reaction with methanesulfonyl chloride in an inert solvent (e.g. chloroform) in the presence of a base (e.g. pyridine) at a low temperature (about $-20°$ - $-10°$ C) to yield the starting compounds (6) (II: X=Cl, Y= $CH_3SO_3$).

The other starting compounds (II) in which the symbols X and Y in the above formulae are other species of halogens or lower alkanesulfonyloxys may also be prepared according to the aforementioned reaction scheme.

Representative of the starting compounds (II) are:

3-butenyl N-methyl-N-(2-chloroethyl)-N'-(2-methanesulfonyloxyethyl)phosphorodiamidate, 3-butenyl N-isopropyl-N-(2-chloroethyl)-N'-(2-methanesulfonyloxyethyl)phosphorodiamidate,
3-pentenyl N-butyl-N-(2-chloroethyl)-N'-(2-methanesulfonyloxyethyl)phosphorodiamidate,
4-phenyl-3-butenyl N-methyl-N-(2-bromoethyl)-N'-(2-ethanesulfonyloxyethyl)phosphorodiamidate,
5-phenyl-3-pentenyl N-methyl-N-(chloroethyl)-N'-(2-propanesulfonyloxyethyl)phosphorodiamidate,
4,4-diphenyl-3-butenyl N-ethyl-N-(2-iodoethyl)- N'-(2-methanesulfonyloxyethyl)phosphorodiamidate, and the like.

The reaction of this invention is carried out in a conventional manner for ozone oxidation using a usual apparatus for ozone oxidation. For example, the starting compounds (II) are dissolved in a suitable solvent, and ozone, or oxygen or air containing ozone may be introduced into the solution at room temperature, or if required under cooling. The suitable solvent involves those usually used in ozonization, for example, methyl chloride, ethyl chloride, chloroform, dichloromethane, dichloroethane, tetrachloroethane, petroleum ether, hexane, cyclohexane, petroleum benzin, ligroin, benzene, toluene, tetrahydrofuran, dioxane, acetone, methyl ethyl ketone, or a mixture of them with or without water. The reaction mixture containing ozone is usually kept at room temperature or under cooling (from $-35°$ C - $-20°$ C) for a period of from several hours to several days. In this reaction, it is appropriate to add a peroxide (e.g. hydrogen peroxide) into the reaction mixture in some cases after the introduction of ozone, but the addition of peroxide is not always an essential procedure. The resulting products (I) may be isolated from the reaction mixture and purified in a conventional manner such as extraction, distillation, chromatography, recrystallization and so on.

Representative of the objective compounds (I) are:

2-[N-methyl-N-(2-chloroethyl)amino]-3-(2-methanesulfonyloxyethyl)-4-hydroperoxy-tetrahydro-2H-1,3,2-oxazaphosphorine 2-oxide,
2-[N-ethyl-N-(2-chloroethyl)amino]-3-(2-methanesulfonyloxyethyl)-4-hydroperoxy-tetrahydro-2H-1,3,2-oxazaphosphorine 2-oxide,
2-[N-isopropyl-N-(2-chloroethyl)amino]-3-(2-methanesulfonyloxyethyl) -4-hydroperoxy-tetrahydro-2H-1,3,2-oxazaphosphorine 2-oxide,
2-[N-butyl-N-(2chloroethyl)amino]-3-(2-methanesulfonyloxyethyl)-4-hydroperoxy-tetrahydro-2H-1,3,2-oxazaphosphorine 2-oxide,
2-[N-methyl-N-(2-bromoethyl)amino]-3-(2-ethanesulfonyloxyethyl)-4-hydroperoxy-tetrahydro-2H-1,3,2-oxazaphosphorine 2-oxide,
2-[N-methyl-N-(2-chloroethyl)amino]-3-(2-propanesulfonyloxyethyl)-4-hydroperoxy-tetrahydro-2H-1,3,2-oxazaphosphorine 2-oxide,
2-[N-ethyl-N-(2-iodoethyl)amino]-3-(2-methanesulfonyloxyethyl)-4-hydroperoxy-tetrahydro-2H-1,3,2-oxazaphosphorine 2-oxide, and the like.

As mentioned above, the compounds (I) produced in this invention are useful as antitumor agents and immunosuppresive agents. For example, the antitumor activity of the representative compound (I), i.e., 2-[N-methyl-N-(2-chloroethyl)amino]-3-(2-methanesulfonyloxyethyl)-4-hydroperoxy-tetrahydro-2H-1,3,2-oxazaphosphorine 2-oxide (hereinafter referred to as Compound Ia), against L-1210 was compared with a commercially available antitumor agent, cyclophosphamide, as indicated in Table I. Table I. Antitumor activity against L-1210

| Test Compound | Route | $ILS_{30}$ (mg/Kg) | Survivors over 30 days (optimal dose mg/Kg) |
|---|---|---|---|
| Cyclophosphamide | p.o. | 35 | 8/8(200) |
|  | i.v. | 25 | 6/7(200) |
| Compound Ia | p.o. | 10 | 8/8(50–200) |
|  | i.v. | 2 | 8/8(25–50) |

Note:
$ILS_{30}$ = 30% Increase of lifespan over control
p.o. = oral administration
i.v. = intravenous injection

Test Method

The test was carried out by means of $BDF_1$ mice. The test compounds were administered from the day following intraperitoneal inoculation of 500,000 cells of L-1210. The animals were observed after 30 days, and the ILS% was calculated from the survival time and the number of survivors.

As seen from Table I, Compound Ia is 3.5 – 12 times more active than cyclophosphamide in in vivo activity against L-1210.

Further, the immune suppression activity of the Componds (I) was compared with a commercially available immnosuppressive agent, cyclophosphamide. Table II indicates the results of test.

Test Method

To a group of ICR female mice, sheep red blood cells ($10^8$/mouse) were intraperitoneally injected for immunization. Test compounds were also intraperitoneally administered at the time of immunization, and their antisera were separated. Hemagglutination titer of the antisera was measured according to the microtiter method, and expressed as $\log_2$ reciprocals of the end point dilution. The antibody resistant to 2-mercaptoethanol was determined similarly after treating the separated antisera with 0.1M 2-mercaptoethanol.

Table II

| | | Effect on antibody formation to sheep red blood cells in mice | | | |
|---|---|---|---|---|---|
| | Dose | Day + 4 | | Day + 7 | |
| Test Compound | (mg/Kg) | Total | 2ME-resist. | Total | 2ME-resist. |
| Saline | — | 8.0 ± 0.7 | 0.6 ± 0.4 | 8.1 ± 0.5 | 6.5 ± 0.5 |
| Cyclophosphamide | 70 | 1.2 ± 1.1 | — | 6.7 ± 0.6 | 5.3 ± 0.6 |
| Compound Ia | 70 | 0.3 ± 0.7 | — | 0 | 0 |
| | 35 | 0.8 ± 1.4 | 0.2 ± 0.5 | 3.0 ± 3.6 | 1.0 ± 0.5 |
| | 17.5 | 2.9 ± 1.6 | 0 | 8.3 ± 1.2 | 6.8 ± 0.6 |

Note:
2ME-resist. = 2-Mercaptoethanol resistant

Acute toxicity of Compound Ia is $LD_{50}$ (in mice) = 284 mg/Kg.

Test Method

The compound was orally administered as a suspension in a vehicle to $BDF_1$ male mice, 40 days old weighing 22 – 23 g. The animals were observed for 21 days, and $LD_{50}$ was calculated by Probid's method.

The cyclic phosphamide derivatives (I) produced in this invention can be administered alone or in combination with pharmaceutically acceptable carriers, the choice of which depends on the preferred route of administration, solubility of the materials, and pharmaceutical practice. In general, the dosage of the compounds (I) is approximately of the same order as the practical dosage of cyclophosphamide, that is, they may be administered in single or divided doses containing from 50 mg to 500 mg of the active ingredient. Practical examples of pharmaceutical preparations with the compounds (I) are tablets, capsules, pills, suspensions, emulsion, solutions, suppositories, ointments, granules, and powders.

The invention will be better explained by the following examples which are not intended as a limitation thereof.

EXAMPLE

Into a solution of 6.2 g of 3-butenyl N-methyl-N-(2-chloroethyl)-N'-(2-methanesulfonyloxyethyl)phosphorodiamidate in 30 ml of aqueous acetone (acetone : water = 1 : 1) is introduced 2 g of ozone within a period of 37 minutes under ice-cooling. Then, 5ml of 30% hydrogen peroxide is added thereto, and the mixture is kept at 0° C for 2 days. The reaction mixture is then condensed under reduced pressure, and the residual aqueous layer is extracted with chloroform. The extract is dried over anhydrous sodium sulfate, and evaporated to dryness. The residue is adsorbed on a column of silica gel, eluated with a mixture of acetone and chloroform (1 : 1), and then recrystallized from an acetone - ether mixture to give 670mg of 2-[N-methyl-N-(2-chloroethyl)amino]-3-(2-methanesulfonyloxyethyl)-4-hydroperoxytetrahydro-2H-1,3,2-oxazaphosphorine 2-oxide as colourless prisms having mp. 119° –121° C (dec).

We claim:

1. A compound of the general formula:

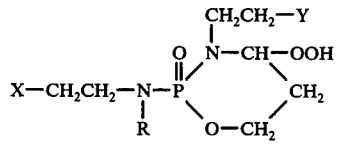

wherein X represents a halogen atom, Y represents a lower alkanesulfonyloxy of 1–5 carbon atoms, and R represents a lower alkyl of 1–5 carbon atoms.

2. A compound claimed in claim 1, said compound being 2-[N-methyl-N-(2-chloroethyl)amino]-3-(2-methanesulfonylozyethyl)-4-hydroperoxy-tetrahydro-2H-1,3,2-oxazaphosphorine 2-oxide.

* * * * *